(12) United States Patent
Clerc et al.

(10) Patent No.: US 9,155,643 B2
(45) Date of Patent: Oct. 13, 2015

(54) APPARATUS AND METHOD FOR MANUFACTURING A SINGLE WIRE STENT

(75) Inventors: Claude Clerc, Marlborough, MA (US); Alexander Turovsky, Latham, NY (US); Michael E. Zupkofska, Rockland, MA (US); Christopher Dubois, Lincoln, RI (US); Mark Wood, Shrewsbury, MA (US); Gary Jordan, Litchfield, NH (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1196 days.

(21) Appl. No.: 13/092,762

(22) Filed: Apr. 22, 2011

(65) Prior Publication Data

US 2011/0265908 A1    Nov. 3, 2011

Related U.S. Application Data

(60) Provisional application No. 61/330,068, filed on Apr. 30, 2010.

(51) Int. Cl.
*A61F 2/90* (2013.01)
*D04C 1/06* (2006.01)
*D04C 3/48* (2006.01)
*D04C 7/00* (2006.01)

(52) U.S. Cl.
CPC ... *A61F 2/90* (2013.01); *D04C 1/06* (2013.01); *D04C 3/48* (2013.01); *D04C 7/00* (2013.01); *A61F 2230/0078* (2013.01); *A61F 2240/001* (2013.01); *A61F 2250/0039* (2013.01); *D10B 2509/06* (2013.01); *Y10T 29/49998* (2015.01)

(58) Field of Classification Search
USPC .................. 140/92.3–92.5, 93 R, 102, 102.5
See application file for complete search history.

(56) References Cited

U.S. PATENT DOCUMENTS

| 4,130,046 A | 12/1978 | Sokol |
| 4,202,718 A | 5/1980 | Mizutani et al. |
| 4,655,771 A | 4/1987 | Wallsten |

(Continued)

FOREIGN PATENT DOCUMENTS

| EP | 0150566 | 8/1985 |
| EP | 1849440 | 10/2007 |

(Continued)

OTHER PUBLICATIONS

PCT International Search Report and Written Opinion mailed Aug. 16, 2010 for PCT Application No. PCT/US2010/022082.

(Continued)

*Primary Examiner* — Shelley Self
*Assistant Examiner* — Pradeep C Battula
(74) *Attorney, Agent, or Firm* — Seager, Tufte & Wickhem LLP

(57) ABSTRACT

A mandrel for manufacturing a stent from a single wire includes a cylindrical member having a plurality of pins at a proximal end region, a plurality of pins at a distal end region, and a plurality of indentations between the proximal pins and the distal pins. These indentations form a helical pattern on the outer surface of the cylindrical member. The single wire is wrapped around every proximal pin and distal pin on the mandrel by following the indentations in the mandrel. The single wire is slid through the indentation under any crossing section of wire and over the next crossing section of wire in an under-over pattern.

17 Claims, 16 Drawing Sheets

(56) References Cited

U.S. PATENT DOCUMENTS

| | | |
|---|---|---|
| 4,893,543 A | 1/1990 | Phillips |
| 5,476,027 A | 12/1995 | Uchida et al. |
| 5,501,133 A | 3/1996 | Brookstein et al. |
| 5,628,787 A | 5/1997 | Mayer |
| 5,630,840 A | 5/1997 | Mayer |
| 5,725,570 A | 3/1998 | Heath |
| 5,800,511 A | 9/1998 | Mayer |
| 5,800,519 A | 9/1998 | Sandock |
| 5,824,077 A | 10/1998 | Mayer |
| 6,007,574 A | 12/1999 | Pulnev et al. |
| 6,240,978 B1 | 6/2001 | Gianotti |
| 6,258,114 B1 | 7/2001 | Konya et al. |
| 6,287,331 B1 | 9/2001 | Heath |
| 6,290,721 B1 | 9/2001 | Heath |
| 6,309,415 B1 | 10/2001 | Pulnev et al. |
| 6,322,576 B1 * | 11/2001 | Wallace et al. ............. 606/191 |
| 6,497,709 B1 | 12/2002 | Heath |
| 6,520,983 B1 | 2/2003 | Colgan et al. |
| 6,527,802 B1 | 3/2003 | Mayer |
| 6,530,949 B2 | 3/2003 | Konya et al. |
| 6,622,604 B1 | 9/2003 | Chouinard et al. |
| 6,641,608 B1 | 11/2003 | Pulnev |
| 6,792,979 B2 * | 9/2004 | Konya et al. ............. 140/92.1 |
| 7,018,401 B1 | 3/2006 | Hyodoh et al. |
| 7,048,014 B2 | 5/2006 | Hyodoh et al. |
| 7,160,323 B2 | 1/2007 | Pulnev et al. |
| 7,419,502 B2 | 9/2008 | Pulnev et al. |
| 7,419,503 B2 | 9/2008 | Pulnev et al. |
| 7,462,192 B2 | 12/2008 | Norton et al. |
| 7,655,039 B2 | 2/2010 | Leanna et al. |
| 7,857,844 B2 | 12/2010 | Norton et al. |
| 7,993,387 B2 | 8/2011 | Clerc et al. |
| 8,109,988 B2 | 2/2012 | Leanna et al. |
| 8,151,682 B2 | 4/2012 | Lilburn et al. |
| 8,459,164 B2 | 6/2013 | Lilburn et al. |
| 8,677,874 B2 | 3/2014 | Lilburn et al. |
| 2002/0147489 A1 | 10/2002 | Hong et al. |
| 2005/0049682 A1 | 3/2005 | Leanna et al. |
| 2005/0256563 A1 | 11/2005 | Clerc et al. |
| 2006/0116752 A1 | 6/2006 | Norton et al. |
| 2006/0190075 A1 | 8/2006 | Jordan et al. |
| 2006/0276887 A1 * | 12/2006 | Brady et al. ............. 623/1.53 |
| 2007/0119295 A1 | 5/2007 | McCullagh et al. |
| 2009/0157158 A1 * | 6/2009 | Ondracek et al. ............. 623/1.2 |
| 2009/0198315 A1 | 8/2009 | Boudjemline |
| 2010/0191319 A1 | 7/2010 | Lilburn et al. |
| 2013/0144372 A1 | 6/2013 | Wood et al. |
| 2014/0074220 A1 | 3/2014 | Clerc et al. |
| 2014/0081382 A1 | 3/2014 | Leanna et al. |
| 2014/0088688 A1 | 3/2014 | Lilburn et al. |

FOREIGN PATENT DOCUMENTS

| | | |
|---|---|---|
| WO | 98/50102 | 11/1998 |
| WO | 00/61464 | 10/2000 |
| WO | 2010/042879 | 4/2010 |

OTHER PUBLICATIONS

PCT International Search Report and Written Opinion mailed Aug. 2, 2011 for PCT Application No. PCT/US11/33634.

* cited by examiner

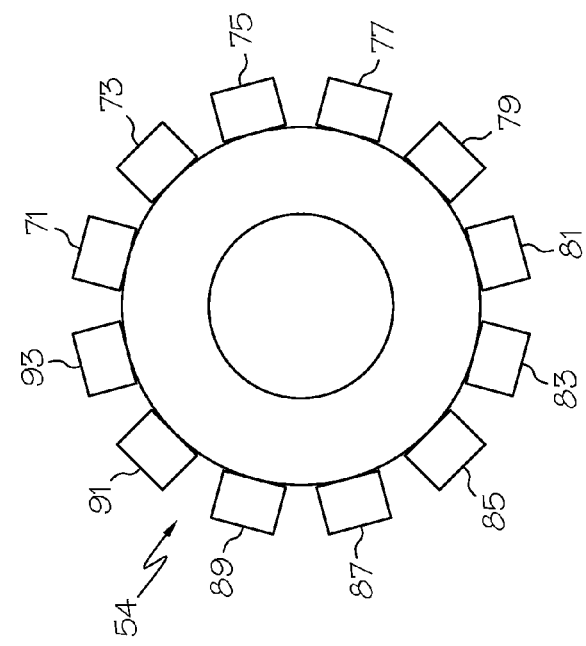
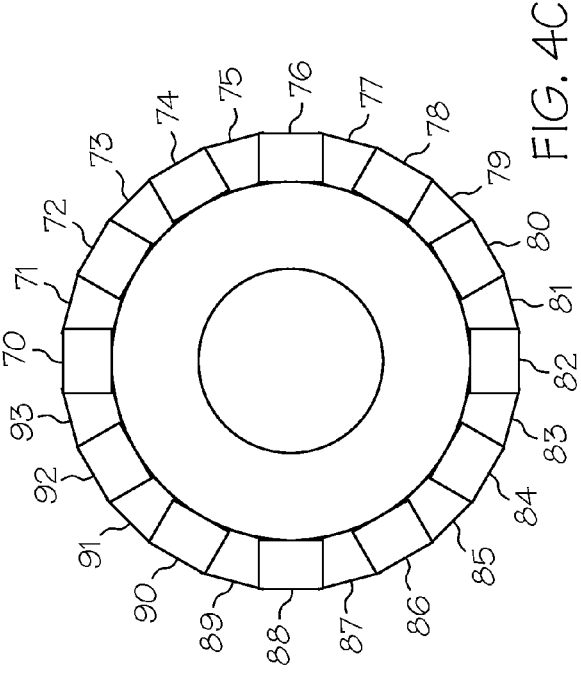
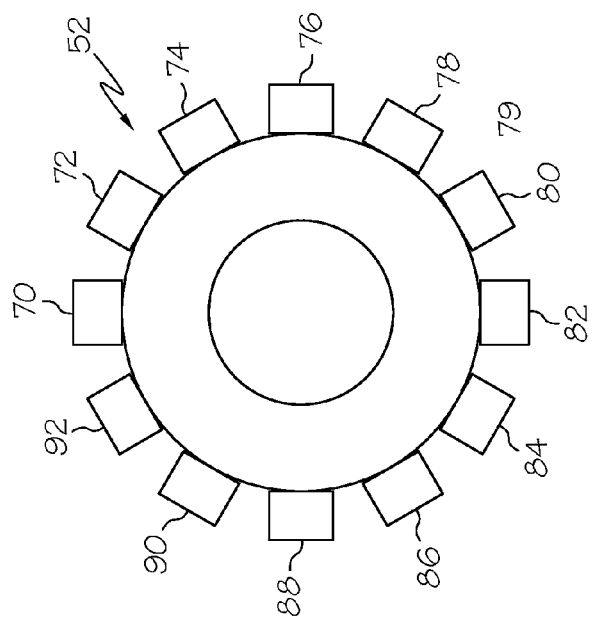

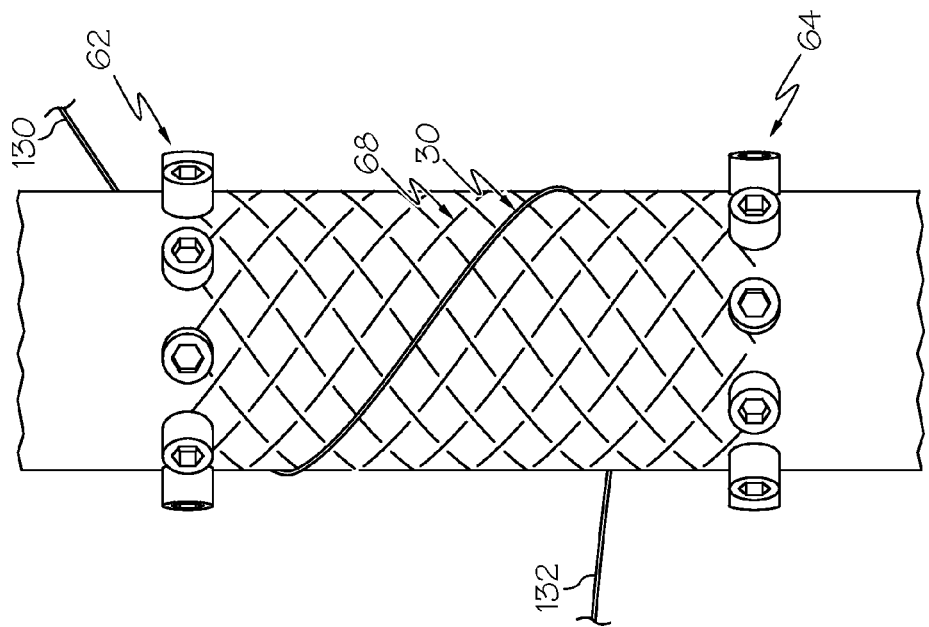
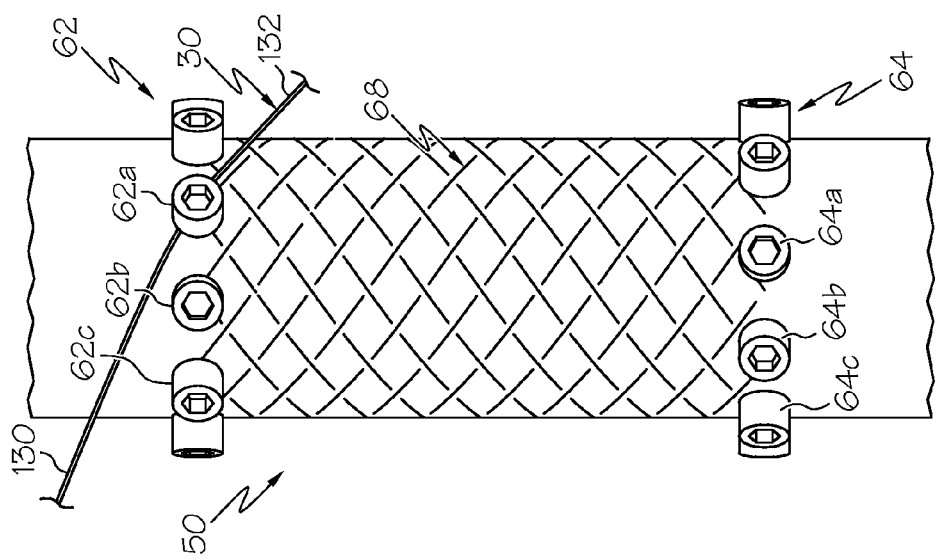

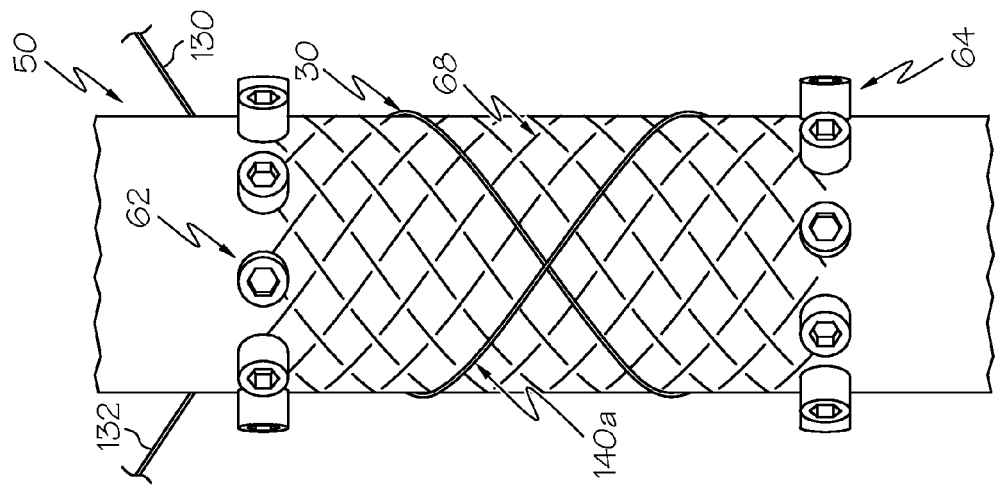
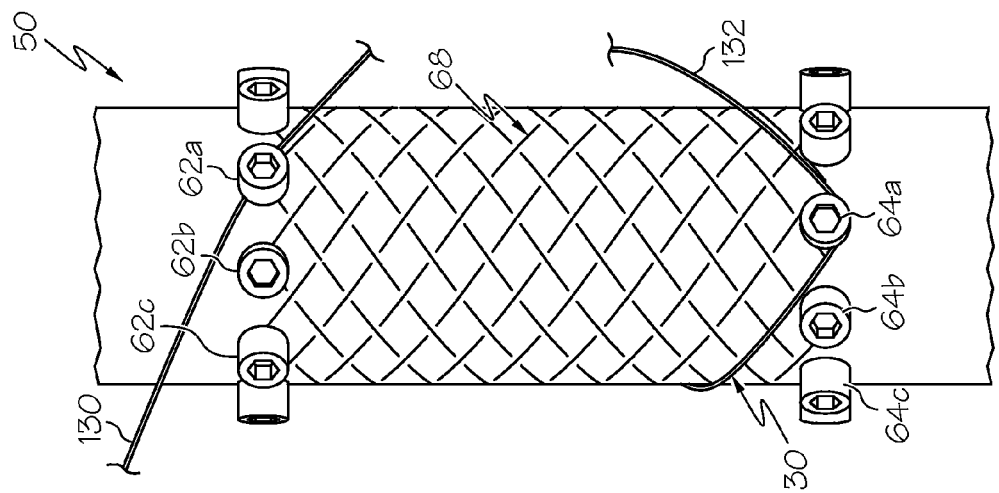

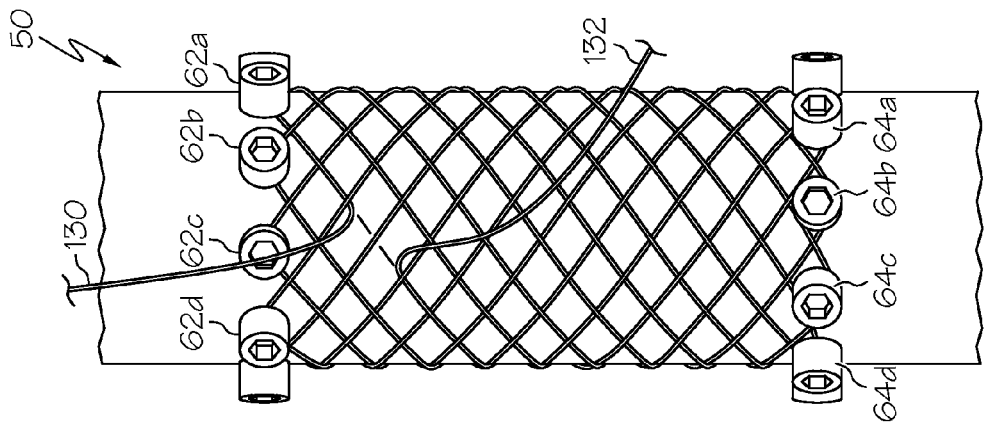
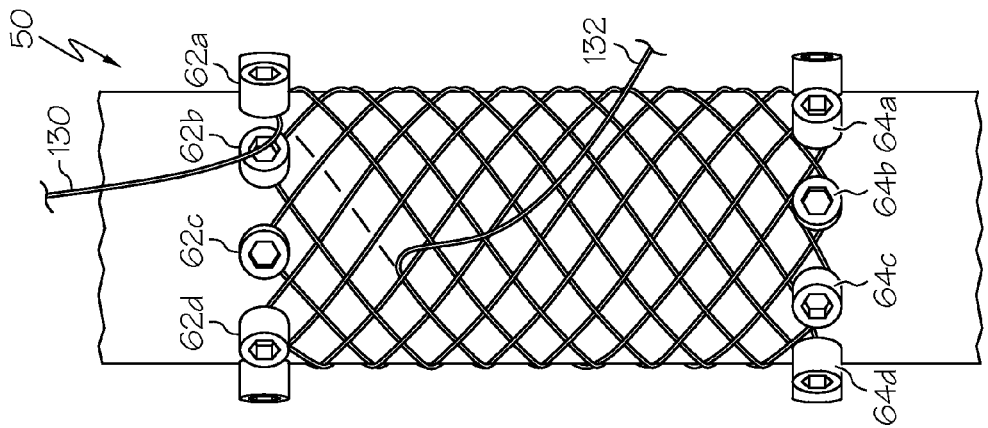

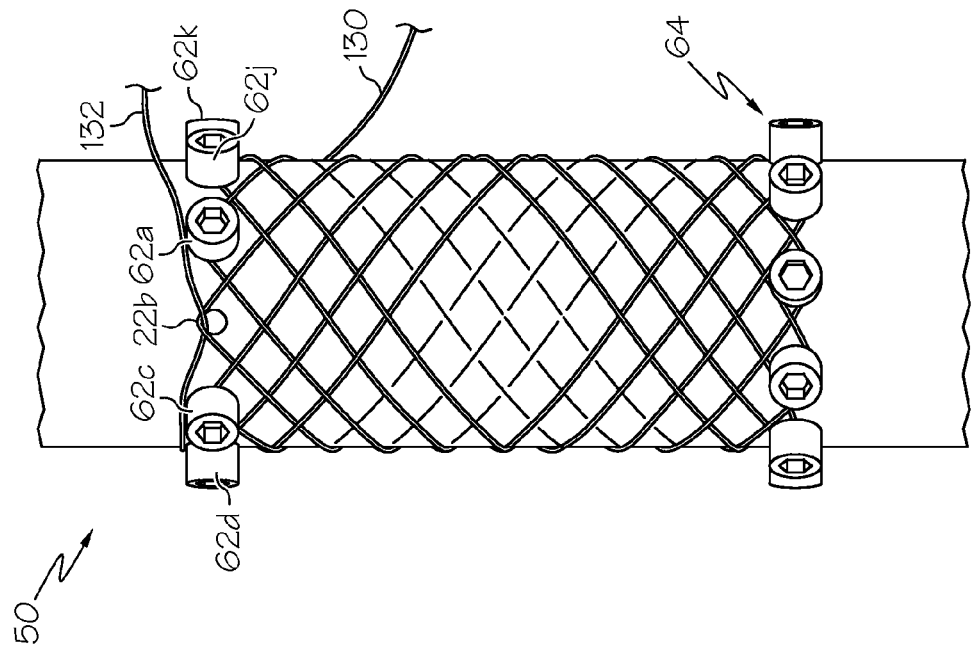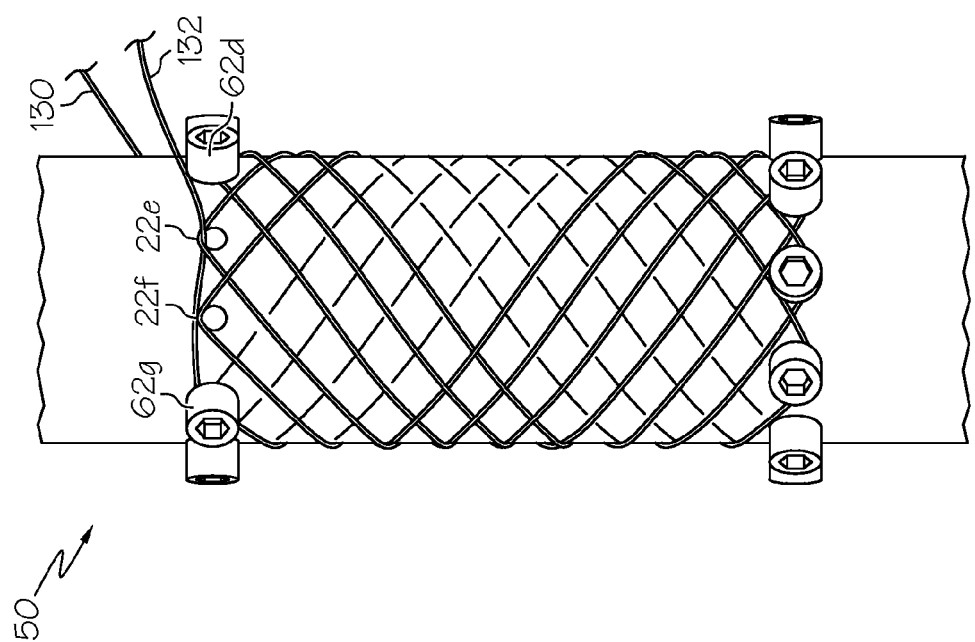

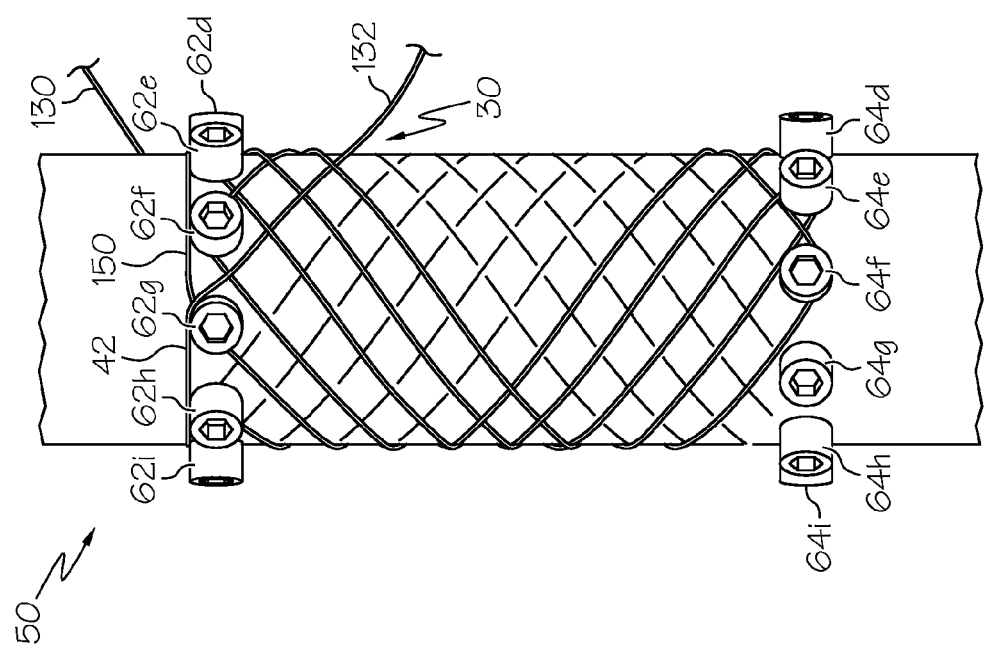

APPARATUS AND METHOD FOR MANUFACTURING A SINGLE WIRE STENT

CROSS-REFERENCE TO RELATED APPLICATIONS

This application claims the benefit of U.S. Provisional Application No. 61/330,068, filed on Apr. 30, 2010, the contents of which is hereby incorporated by reference.

BACKGROUND

Stents are well known in the art for treating stenoses in numerous ducts, vessels, or lumens of anatomy, such as within vascular and gastrointestinal systems, urinary tracts, bile ducts, fallopian tubes, coronary vessels, secondary vessels, etc. Stents may be expandable by an internal radial force (such as a balloon), self-expanding, or a combination of self-expanding and balloon expandable (hybrid expandable).

While various methods may be used to manufacture a stent, in some instances, stents may be woven or braided using a single wire or a plurality of wires. These wires may be made from a variety of biocompatible materials, such as nitinol wire, PET, PTFE, or other polymeric materials. After forming the stent, the stent may remain bare or may be partially or fully covered with other materials.

BRIEF SUMMARY

This disclosure concerns a mandrel and method of manufacturing single wire braided stents on the mandrel that controls the geometry while increasing efficiency of manufacture. In a representative embodiment of the invention, the stent made using this mandrel and method has a proximal end, a distal end, a diameter, a length, a plurality of loops on the proximal end, and a plurality of loops on the distal end.

In one embodiment, the mandrel comprises a cylindrical member having an outer surface extending longitudinally from a proximal end region to a distal end region. In at least one embodiment, the mandrel further comprises proximal pins extending radially outward from the outer surface of the cylindrical member at the proximal end region. In at least one embodiment, the proximal pins are distributed substantially equidistant from one another along the circumference of the mandrel. In at least one embodiment, the mandrel also has distal pins extending radially outward from the outer surface of the cylindrical member at the distal end region. In at least one embodiment, the distal pins are also distributed substantially equidistant from one another along the circumference of the mandrel. In at least one embodiment, each distal pin is circumferentially positioned between two proximal pins. In at least one embodiment, the outer surface also has a plurality of indentations between the proximal pins and the distal pins. In at least one embodiment, these indentations form a helical pattern on the outer surface of the cylindrical member.

In at least one embodiment, to manufacture the stent using the mandrel, a single wire is wrapped around a first proximal pin and down the mandrel in a downward helical direction, following a first plurality of indentations until the single wire reaches a first distal pin. The wire is wrapped around the first distal pin and up the mandrel in an upward helical direction by following a second plurality of indentations on the mandrel until the single wire reaches a second proximal pin. In at least one embodiment, the wire slides under a first crossing wire. In at least one embodiment, the single wire is then wrapped around the second proximal pin and down the mandrel in a downward helical direction by following a third plurality of indentations until the single wire reaches a second distal pin. In at least one embodiment, the wire slides under the first crossing section of wire and then over at least a second crossing section of wire in an under-over pattern. In at least one embodiment, this process is repeated until the single wire has wrapped around every proximal pin and distal pin on the mandrel by following the indentations in the mandrel, sliding the single wire under any crossing section of wire and over the next crossing section of wire in the under-over pattern.

In another embodiment, the mandrel and method of manufacturing may be used to form a single-wire flared stent having a proximal end, a distal end, a major outer diameter at the proximal end and at the distal end, a minor outer diameter between the proximal end and the distal end, a length, a plurality of loops on the proximal end, and a plurality of loops on the distal end. In at least one embodiment, the same method for manufacturing the stent on the mandrel as previously described may also be used to manufacture the flared stent.

BRIEF DESCRIPTION OF THE SEVERAL VIEWS OF THE DRAWING(S)

FIG. 4A is a top view of the mandrel shown in FIG. 2.

FIG. 4B is a bottom view of the mandrel shown in FIG. 2

FIG. 4C is FIG. 4A superimposed on FIG. 4B.

FIGS. 7A-7C show an embodiment of the method of manufacturing the retrieval loop of the stent of FIG. 1 using the mandrel of FIG. 2.

DETAILED DESCRIPTION

Figure 1:
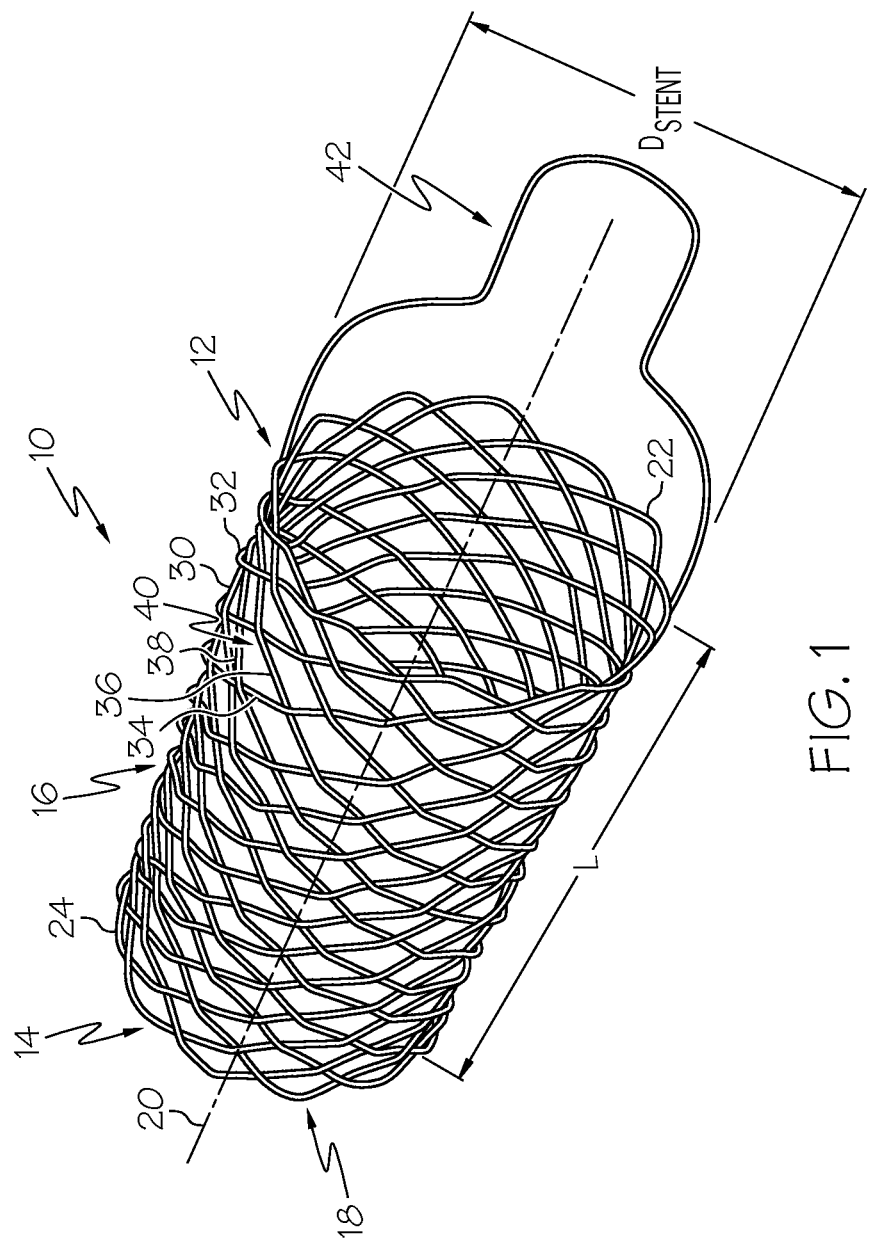
FIG. 1 is a perspective view of an embodiment of the stent, the stent optionally having a retrieval loop.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

An embodiment of a stent made using the mandrel and manufacturing method described in this disclosure is shown in FIG. 1. Stent 10 is defined at least by its desired overall length L, diameter D, and number of crossing wires. For example, stent 10 can be a 40 mm×20 mm 24-wire stent with a desired overall length L that is 40 mm and a diameter D of 20 mm with 24 crossing wires. For purposes of this disclosure, "wire" is interchangeable with "strand," "filament," and other like terms. It should be understood that, for purposes of this disclosure, an exemplary "24-wire stent" is made from a single wire to form a stent with twenty-four crossing wires in a braided configuration.

In the embodiment shown in FIG. 1, stent 10 has proximal end 12, distal end 14, braided surface 16, loops 18, and longitudinal axis 20. Stent 10 is a tubular member having diameter D and braided surface 16 that extends along longitudinal axis 20 for a length L from proximal end 12 to distal end 14. A plurality of loops 18 are formed at both proximal end 12 and distal end 14. The total number of loops 18 is equivalent to the total number of crossing wires in stent 10 that form braided surface 16. For example, a 24-wire stent would have twenty-four total loops 18, and a 30-wire stent would have thirty total loops 18. In the embodiment shown in FIG. 1, half of loops 18 are proximal loops 22 (located at proximal end 12) and half of loops 18 are distal loops 24 (located at distal end 14). In this embodiment, proximal loops 22 are circumferentially located between distal loops 24 and axially separated therefrom, meaning a proximal loop 22 is not axially aligned with a distal loop 24.

In at least one embodiment, braided surface 16 and loops 18 are formed from a single wire 30. In some embodiments, wire 30 is comprised of metals, polymers, composites and other materials, such as nitinol, PET, PTFE, and other biocompatible materials. In some embodiments, wire 30 is a cored wire, such as a nitinol wire with a platinum core and other cored wires like those described in U.S. Pat. Nos. 5,628,787; 5,630,840; 5,725,570; 5,800,511; 5,824,077; 6,287,331; 6,290,721, 6,497,709, 6,527,802; and 7,101,392, the entire contents of which are hereby incorporated herein by reference. While the disclosure below describes an embodiment using a round wire, wires of different cross-sections can be used (such as flat wires, square wires, triangular wires, etc.) and the equations provided herein can be modified accordingly. The wire can also have varying flexibility characteristics and varying wire diameter throughout the stent as desired. The wire may have radiopacity characteristics. The wire can also be fully or partially coated with a substance, including but not limited to a drug, genetic material, cells, a non-genetic therapeutic agent, a polymer matrix having a therapeutic component or any other substance which it would desirable to deliver into a body lumen.

In at least one embodiment (as shown in FIG. 1), braided surface 16 has an under-over pattern of crossing wires 32, 34, 36, 38 such that wire 30 alternates from passing under a first crossing wire 32 to overlapping a second crossing wire 34. The intersections of four crossing wires 32, 34, 36, 38 form a diamond-like shape 40 called a lozenge. A plurality of lozenges 40 makes up braided surface 16, as shown in FIG. 1.

At least one embodiment of stent 10 optionally includes a retrieval loop 42 at proximal end 12, which is shown in FIG. 1. After stent 10 is deployed in a lumen, retrieval loop 42 can be used to reposition, remove or retrieve stent 10 from the lumen. The retrieval loop design shown in FIG. 1 is exemplary, and other options exist for retrieval loops and other features used to reposition, removing or retrieving the stent from the lumen. In at least one embodiment, retrieval loop 42 is formed concurrently with the rest of stent 10 from wire 30, as will be discussed with respect to FIGS. 7A-7C.

Figure 2:
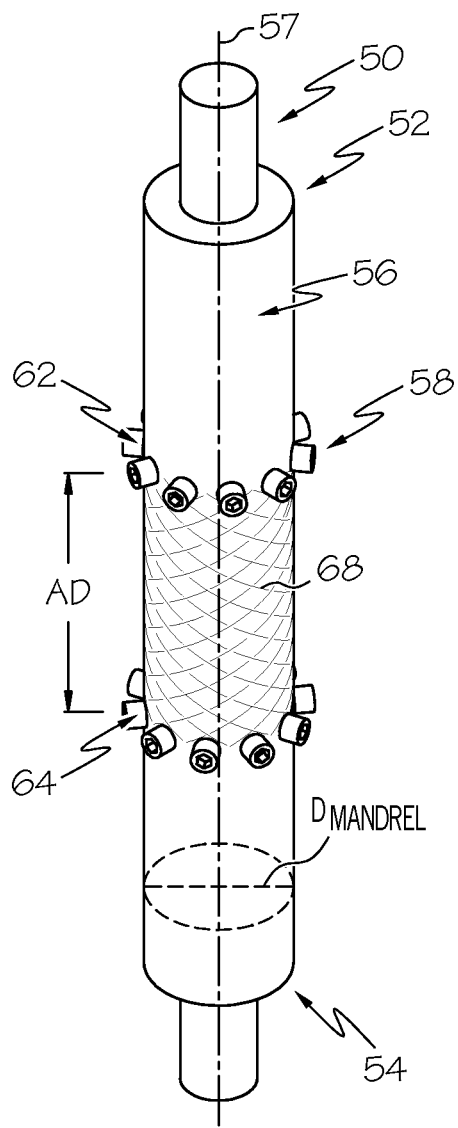
FIG. 2 is a perspective view of an embodiment of the mandrel used to form the stent shown in FIG. 1.

In order to manufacture stent 10, single wire 30 can be wrapped around mandrel 50, an example of which is shown in FIG. 2. Mandrel 50 can be a solid or hollow cylindrical member having outer diameter $D_{mandrel}$ and made from a metal, polymer, or composite material. To determine the proper outer diameter $D_{mandrel}$ of mandrel 50 for stent 10 having diameter $D_{stent}$, the following equation can be used:

$$D_{mandrel} = D_{stent} - 4d,$$

where d is the diameter (or thickness) of wire 30.

In the embodiment shown in FIG. 2, mandrel 50 has proximal end region 52, distal end region 54, outer surface 56, longitudinal axis 57, and a plurality of pins 58. In this embodiment, mandrel 50 extends from proximal end region 52 to distal end region 54 along longitudinal axis 57, and pins 58 are circumferentially positioned on outer surface 56.

Pins 58 are either fixedly attached to mandrel 50 or adjustably held so that they can be loosened or tightened as needed. The pins shown in FIG. 2 are exemplary and represent only one form of pin. Other pins may include permanent or removable tabs, screws, hooks, and other fasteners. In some embodiments, pins 58 may be held within pin holes or screw holes (not shown).

Although any number of pins 58 can be used, in at least one embodiment (shown in FIG. 1), the total number of pins 58 is equivalent to the total number of loops 18 desired on stent 10. For example, mandrel 50 having twenty-four pins 58 will make stent 10 (shown in FIG. 1) having twenty-four loops 18. Although pins 58 can be positioned in any way, in at least one embodiment, a first plurality of pins 62 ("proximal pins") are radially positioned on the outer surface of the cylindrical member at proximal end region 52 and a second plurality of pins 64 ("distal pins") are radially positioned on the outer surface of the cylindrical member at the distal end region 54. In at least one embodiment, the total number of proximal pins 62 on mandrel 50 is equivalent to the total number of proximal loops 22 desired on stent 10, and the total number of distal pins 64 is equivalent to the total number of distal loops 24 desired on stent 10. In at least one embodiment, the total number of proximal pins 62 is equivalent to the total number of distal pins 64. However, depending on the configuration of stent 10, the total number of proximal pins 62 on mandrel 50 may be greater or less than the total number of distal pins 64. In the embodiment shown in FIG. 2, distal pins 64 are rotationally offset from proximal pins 62 such that first distal pin 64a is circumferentially positioned between first proximal pin 62a and second proximal pin 62b, rather than directly aligned with either first proximal pin 62a or second proximal pin 62b. In at least one embodiment, first distal pin 64a is located at the midpoint between first proximal pin 62a and second proximal pin 62b. In at least one embodiment, distal pins 64 are rotationally offset from proximal pins 62 by an angle, which is determined by dividing 360° by the total number of pins 58. As mentioned above, the pins 58 shown in FIG. 1 are exemplary only. Any number, position, orientation, or combination of pins 58 can be used. While in the embodiment shown, proximal pins 62 are all circumferentially aligned, as are distal pins 64, it is within the scope of the invention that the pins be staggered circumferentially to create staggered end loops on stent 10.

In the embodiment as shown in FIG. 2, proximal pins 62 are separated from distal pins 64 by some axial distance AD between the center of proximal pin 62 and the center of distal pin 64. Axial distance AD can be a function of at least the following parameters: the desired overall length L of stent 10, the number of lozenges 40, the axial length $L_{lozenge}$ of each lozenge 40, the radius of wire 30, and the radius of the pinhole in which pins 58 are held (or, in some cases, the radius of the pin 58 itself). It should be noted that where removable tabs, screws, hooks, and other fasteners are used, the axial distance can be a function of additional parameters.

Figure 3:
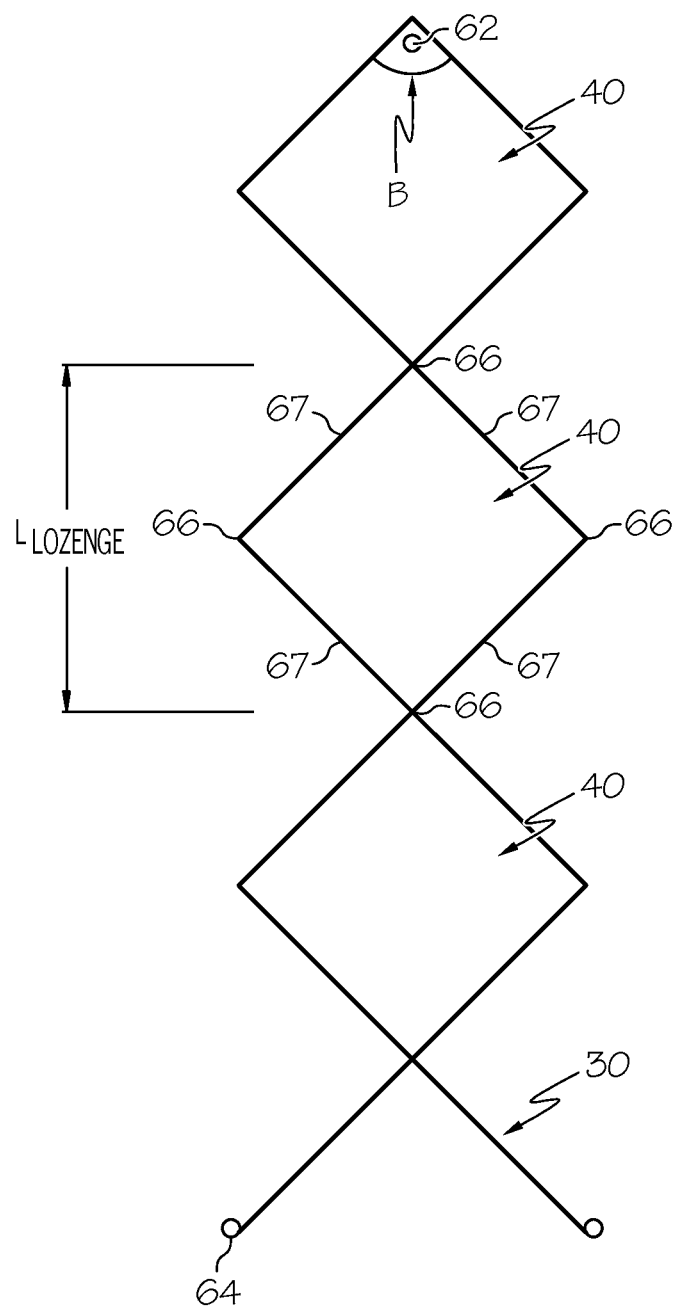
FIG. 3 is a view of a group of lozenges from the stent of FIG. 1.

The number of lozenges 40 and the axial length $L_{lozenge}$ of each lozenge 40 is dependent upon various design parameters of stent 10, including, but not limited to, the desired overall length L and the braid angle B. FIG. 3 shows an illustrative example of a group of lozenges 40. In the embodiment shown, each lozenge 40 is a quadrilateral-shaped (and more specifically, a diamond-shaped) structure having four tips 66 and four sides 67. In the embodiment as shown, the lozenge tips 66 and sides 67 lie in the middle of wire 30, such that the lozenge axial length, $L_{lozenge}$, includes the radius r of wire 30. The lozenge axial length, $L_{lozenge}$, is a function of at least the braid angle B of stent 10. In this embodiment, the number of lozenges, n, is the desired overall length L of stent 10 divided by lozenge axial length, $L_{lozenge}$. The number of lozenges, n, is rounded to the nearest whole number and then adjusted by adding 0.5. This adjustment is necessary for this embodiment because of the configuration of pins 62, 64 (i.e., pin 64a is located at the midpoint between a first proximal pin 62a and a second proximal pin 62b). In instances where the distal pin 64a is located at the midpoint between proximal pin 62a and proximal pin 62b, there will be a half lozenge at the end of each lozenge group, as shown in FIG. 3. Therefore, for this embodiment, the actual axial length $L_{actual}$ of stent 10 is determined using the following equation:

$$L_{actual}=(n+0.5)(L_{lozenge})+2r;$$

where r is the radius of the wire and r=d/2. As a result of this equation, $L_{actual}$ will be greater than the desired length L of stent 10 in the embodiment shown. For example, if desired length L of stent 10 is 40 mm and the lozenge axial length, $L_{lozenge}$, is 3.5 mm, n will be 40 divided by 3.5, which is 11.428 lozenges. n is then rounded to the nearest whole number, which for this example is 11. Assuming a wire radius of 0.1 mm, $L_{actual}=(11+0.5)(3.5$ mm$)+2*(0.1$ mm$)=40.45$ mm. The axial distance AD between proximal pins 62 and distal pins 64 shown in FIG. 2 is then calculated by subtracting two wire radii and two pin hole radii from $L_{actual}$. For example, if the pin hole radius is 0.2 mm, the AD between proximal pins 62 and distal pins 64 will be 40.45 mm−2(0.1 mm)−2(0.2 mm)=39.85 mm.

Referring again to the embodiment of FIG. 2, mandrel 50 has a plurality of cut-outs or indentations 68 on outer surface 56, where material is removed from outer surface 56. The indentations 68 have a desired depth, width and overall shape. The depth of the indentation will typically be no more than the overall width or thickness of wire 30. Indentations 68 are shaped so that the wire can be easily pushed in and out of the indentations. In some embodiments, indentations 68 will have either a "bathtub" shape, a straight cut shape, or any other similar shape. In at least one embodiment, the depth of the indentation 68 is about equal to the diameter d of wire 30. In at least one embodiment, the width of the indentation 68 is slightly larger than the diameter d of wire 30. In some embodiments, the indentations may taper from a maximum depth in the middle of the indentation to a minimum depth at the ends of the indentation. Other configurations of the indentations 68 are within the scope of the invention.

Indentations 68 are positioned at least wherever an intersection of two crossing wires potentially necessitates one crossing wire to slide under the other crossing wire. Indentations 68 serve at least the following purposes. First, indentations 68 indicate at each intersection of crossing wires if the first crossing wire goes over or under the second crossing wire. This is especially useful towards the end of the braiding process where the crossing wires may be held tightly together and open space on mandrel 50 may potentially be limited. In some embodiments, indentations 68 facilitate the braiding of stent 10 in an under-over pattern by allowing wire 30 to easily pass under a crossing wire, which is raised relative to the particular indentation 68 wire 30 passes through. The crossing wire will typically rest on outer surface 56 of mandrel 50 and, since indentation 68 is a depression in the outer surface 56, this creates an opening between a portion of the crossing wire and a surface of the indentation (which is below the outer surface 56). This opening allows wire 30 to pass underneath a crossing wire. As can be seen for example in FIG. 6A, there are three indentations 68 at each location where the crossing wires intersect. Two of the three indentations 68 are aligned on one helical pathway and the third indentation 68 is positioned between the two aligned indentations 68 and aligned on a helical pathway extending in different direction. In some embodiments, indentations 68 can also hold wire 30 in place during the braiding process so that stent 10 will have a regular or controlled geometry, and particularly to ensure that stent 10 is braided at the desired braiding angle B.

While the above discussion focuses on "indentations," it should be noted that, from another viewpoint, the area surrounding "indentations" can be considered to be a raised surface or "raised bump" relative to the "indentation." Thus, it is within the scope of the invention that the surface is raised in certain areas, rather than removed. The surface 56 of mandrel 50 can have many indentations, or the surface could have many raised bumps, or a combination of indentations and raised bumps. The majority of the surface 56 can be smooth or the majority of the surface can be bumpy or rough. The arrangement of the indentations (or raised bumps) will slightly affect the outer diameter of the stent 10 in some embodiments.

Before the manufacturing process can commence, the displacement of pins 58 should be determined. This displacement can be either a negative (−) displacement or a positive (+) displacement of a certain magnitude. FIGS. 4A-4C help to illustrate this. FIG. 4A shows a top view of the mandrel 50 shown in FIG. 2 and only shows proximal pins 62, each proximal pin labeled with an even reference numeral (e.g. 70, 72, 74, 76, 78, 80, 82, 84, 86, 88, 90, 92). FIG. 4B shows a bottom view of the mandrel 50 shown in FIG. 2 and only shows distal pins 64, each distal pin labeled with an odd reference numeral (e.g. 71, 73, 75, 77, 79, 81, 83, 85, 87, 89, 91, 93). FIG. 4C is FIG. 4A superimposed on FIG. 4B so that all pins 58 (both the proximal pins 62 and the distal pins 64) are visible. In at least the embodiment shown, all pins 58 are visible because the proximal pins 62 are rotationally offset from the distal pins 64 on the mandrel 50, as discussed above.

Any of the proximal pins 62 can be used as the first proximal pin 62a, and any of the distal pins 64 can be used as the first distal pin 64a. If the first distal pin 64a is in the clockwise direction of the first proximal pin 62a, this can be considered a negative displacement. If the first distal pin 64a is in the counterclockwise direction of the first proximal pin 62a, this can be considered a positive displacement. For example, referring to FIG. 4C, if pin 70 is chosen as first proximal pin 62a, choosing pin 71 as first distal pin 64a would be a negative displacement, while choosing pin 93 would be a positive displacement. As another example, if pin 82 is chosen as first proximal pin 62a, choosing pin 83 as first distal pin 64a would be a negative displacement, while choosing pin 81 would be a positive displacement.

The displacement also has a magnitude. The only caveat to the selection of the displacement is that the magnitude of the displacement and the total number of pins 58 should be coprime (or "relatively prime") numbers, meaning that their greatest common divisor is equal to 1. If the magnitude of the displacement and the total number of pins 58 are not coprime numbers, wire 30 will wrap around the same set of pins. Therefore, wire 30 will not reach all of the pins, which may be undesirable. For example, for a 24-wire stent, if a displacement of −3 was chosen and pin 70 was chosen as the first proximal pin 62a, wire 30 would wrap around pin 70, then pin 73, then pin 76, then pin 79, 82, 85, 88, 91 and back to pin 70. In this example, the wire would never wrap around the remaining pins (71, 72, 74, 75, 77, 78, 80, 81, 83, 84, 86, 87, 89, 90, 92, 93), which, in some cases, results in an incomplete braiding pattern. If, for example, a displacement of −5 was used for a 24-wire stent, then wire 30 would wrap around pin 70, then 75, 80, 85, 90; then 71, 76, 81, 86, 91, etc. until all of the pins on mandrel 50 in FIG. 4 have been used. For longer stents, the wire 30 may wrap around the mandrel 50 multiple times before reaching the distal pin, however the same geometrical and manufacturing principles apply as discussed above.

Figure 5:
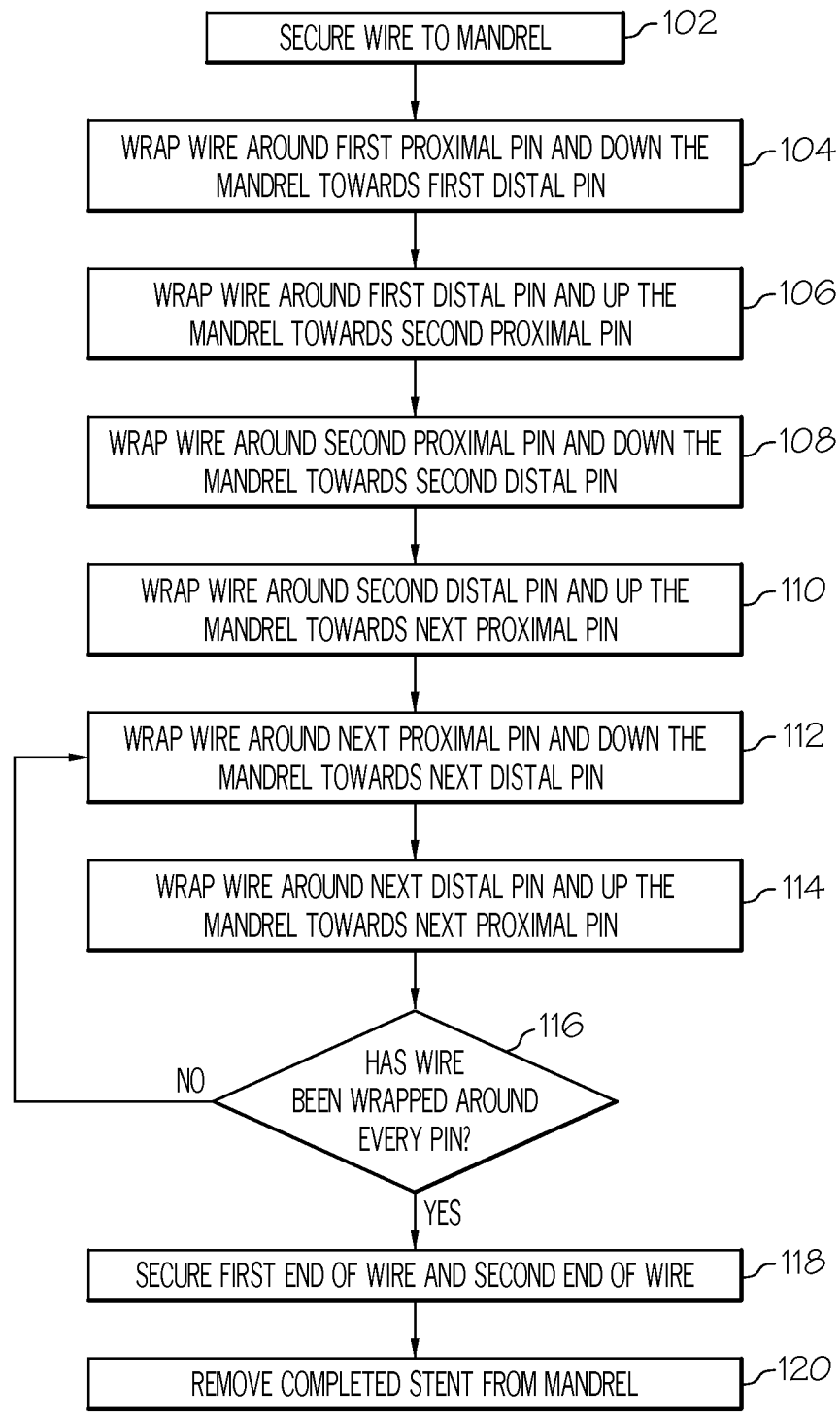
FIG. 5 is a block diagram of at least one embodiment of the method of manufacturing the stent of FIG. 1 using the mandrel of FIG. 2.

FIG. 5 is a block diagram showing an embodiment of a method of making stent 10 using mandrel 50. In order to manufacture the stent 10, a single wire 30 is first secured to the mandrel at step 102. In step 104, wire 30 is wrapped around first proximal pin 62a and down mandrel 50 in a downward helical direction towards first distal pin 64a. As wire 30 is being wrapped down mandrel 50, wire 30 follows the indentations 68 (or, conversely, the raised bumps) in outer surface 56 of mandrel 50 until the wire reaches first distal pin 64a. In step 106, wire 30 is wrapped around the first distal pin 64a and up mandrel 50 in an upward helical direction until wire 30 reaches a second proximal pin 62b. Wire 30 is then wrapped around second proximal pin 62b in step 108 and down mandrel 50 towards second distal pin 64b. In step 110, wire 30 is wrapped around second distal pin 64b and up mandrel 50 in an upward helical direction until wire 30 reaches the next proximal pin 62c. Wire 30 is then wrapped around proximal pin 62c and down mandrel 50 towards next distal pin 62c in step 112. In step 114, wire 30 is wrapped around distal pin 64c and back up mandrel 50 towards the next proximal pin 62d. In this embodiment, steps 112 and 114 are repeated until wire 30 has wrapped around every proximal pin 62 and every distal pin 64 as needed for the desired stent pattern. Both ends of the wire are secured and, in final step 120, the completed stent 10 is removed from mandrel 50.

Figure 6E:
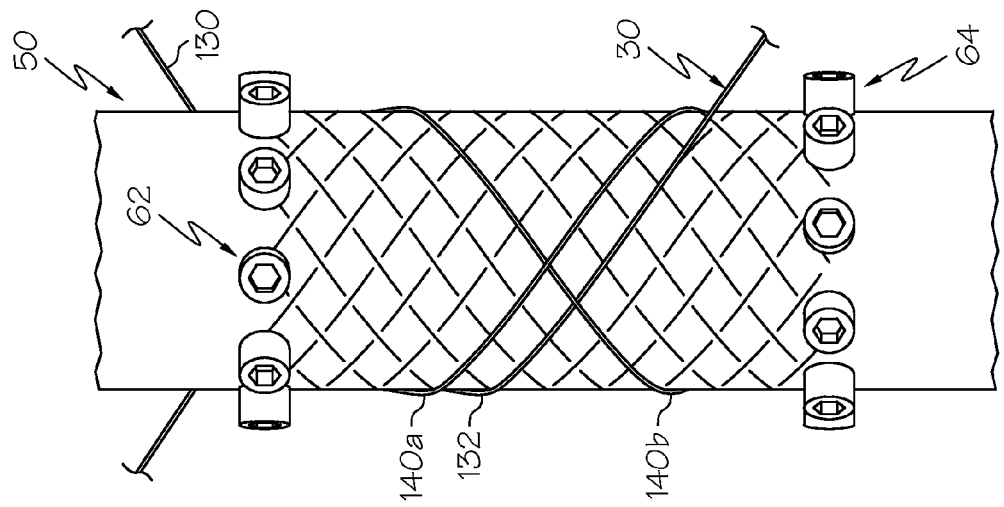
FIGS. 6A-6N show an embodiment of each step of the method of manufacturing the stent of FIG. 1 using the mandrel of FIG. 2, as outlined in the diagram of FIG. 5.
Figure 6F:
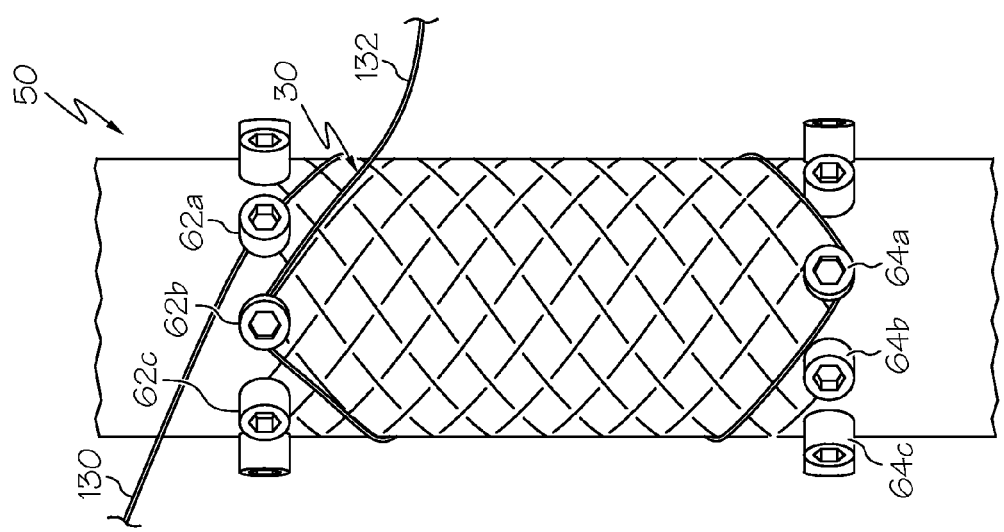
Figure 6H:
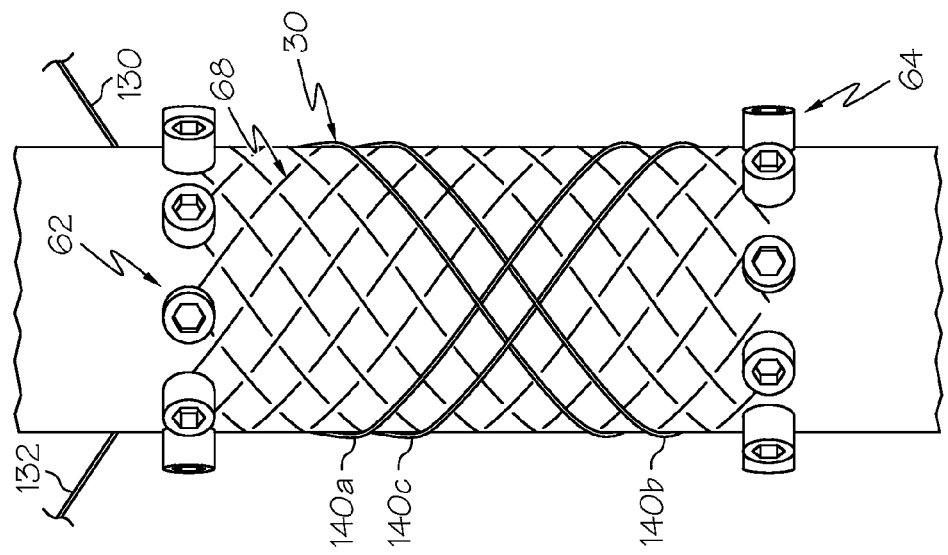
Figure 6G:
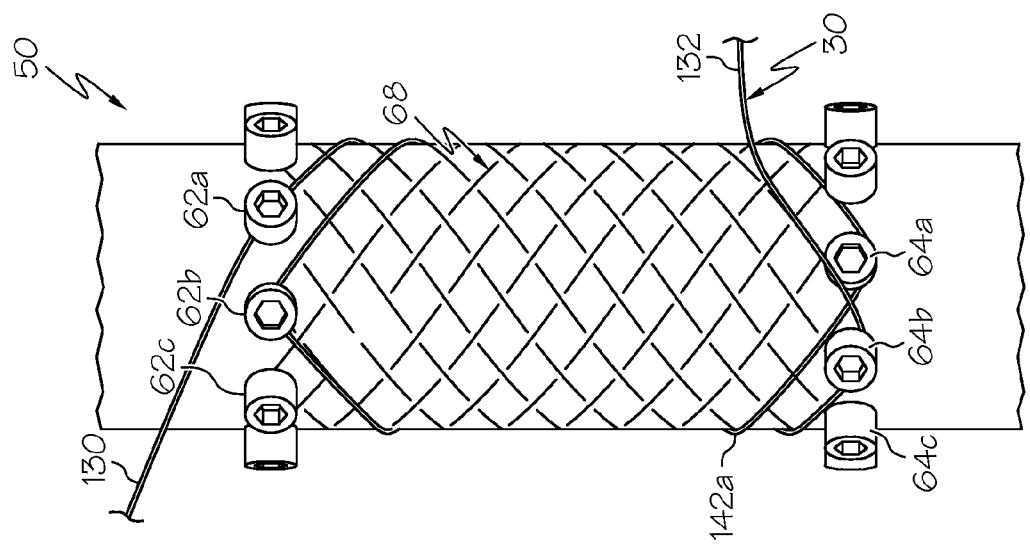
Figure 6J:
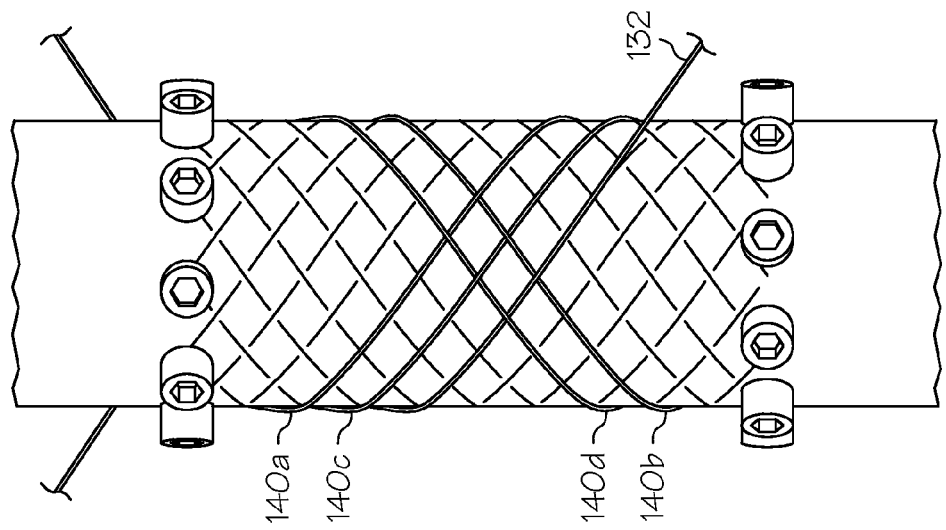
Figure 6I:
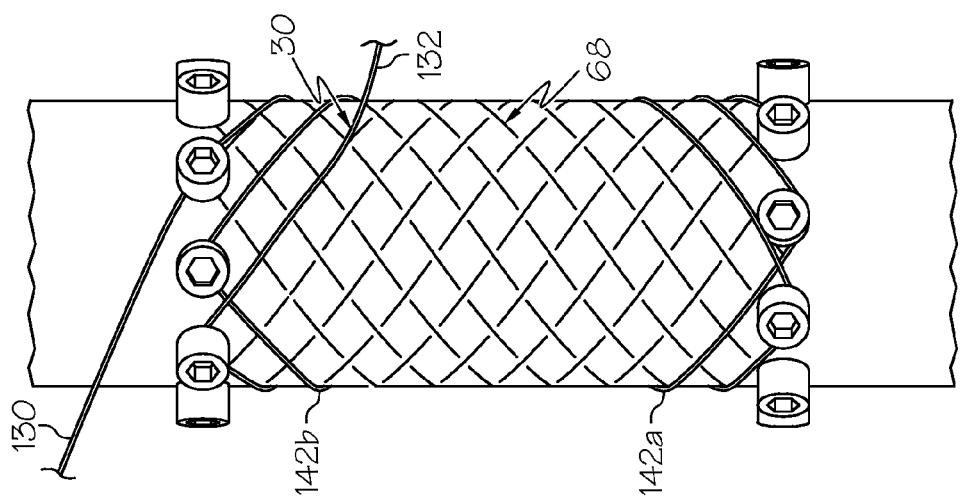
Figure 6N:
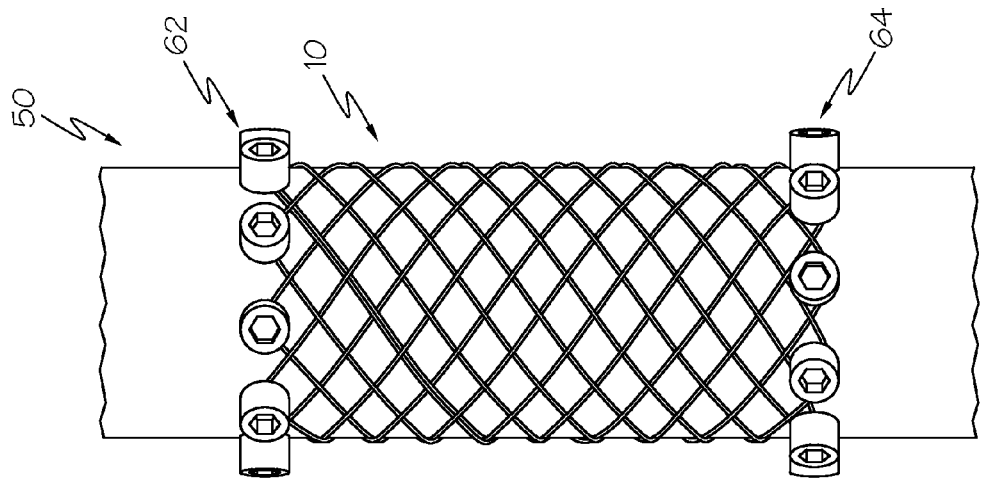

FIGS. 6A-6N show an exemplary embodiment of method steps 102-120 as outlined in FIG. 5. First proximal pin 62a and first distal pin 64a are chosen based on the desired displacement as discussed above with respect to FIG. 4. In the exemplary embodiment shown in FIGS. 6A-6N, this displacement is −1.

In the exemplary embodiment shown in FIG. 6A, wire 30 is first secured to mandrel 50. Wire 30 is placed under first proximal pin 62a, and first proximal pin 62a may be tightened as necessary to hold wire 30 in place. In other embodiments, other methods of securing the wire in place on the mandrel may be used, such has having a separate screw located above the proximal pins 62 to which wire 30 can be secured.

Wire 30 is then wrapped around first proximal pin 62a. In the embodiment shown, a first portion 130 of wire 30 is left above first proximal pin 62a and a second portion 132 of wire 30 left below first proximal pin 62a. Portion 132 of wire 30 is then wrapped around mandrel 50 in a downward helical fashion while following a set of indentations 68, as shown in FIG. 6B (which shows mandrel 50 of FIG. 6A after a 180° turn). In at least one embodiment, wire 30 will make almost one complete wrap around mandrel 50 before it reaches distal pins 64.

As wire 30 reaches distal pins 64 (as shown in FIG. 6C), wire 30 can be at least partially looped around the first distal pin 64a. As wire 30 at least partially loops around first distal pin 64a, wire 30 makes an approximately 90° turn in this embodiment and wraps around mandrel 50 in an upward helical fashion toward proximal pins 62 while following a set of indentations 68. As wire 30 wraps around mandrel 50 toward proximal pins 62 (as shown in FIG. 6D), wire 30 meets a crossing wire 140a that is already in place. In this embodiment, wire 30 goes under first crossing wire 140a by sliding through indentation 68 that passes under first crossing wire 140 at that juncture. Because indentation 68 forms a depression in outer surface 56, first crossing wire 140a will be slightly raised to allow wire 30 to smoothly and easily pass underneath first crossing wire 140a. Wire 30 (and, in particular, portion 132) slides under the first crossing wire 140a and can be pulled through until wire 30 is taut. In the embodiment as described herein, wire 30 must go under the first crossing wire 140a that wire 30 meets. It is within the scope of the invention that, in some embodiments, the braiding pattern may require wire 30 to go over the first crossing wire 140a.

Wire 30 continues to wrap up mandrel 50 until it reaches second proximal pin 62b, in the embodiment shown in FIG. 6E. In this embodiment, wire 30 is then at least partially looped around second proximal pin 62b. Each time wire 30 loops around a pin 62, 64, a loop 18 in stent 10 is formed. In this embodiment, as wire 30 loops at least partially around second proximal pin 62b, wire 30 makes a 90° turn. Wire 30 is wrapped around mandrel 50 again in a downward helical fashion toward distal pins 64 while following a set of indentations 68 until it reaches second distal pin 64b. As shown in FIG. 6F, wire 30 follows another set of indentations 68 and goes under first crossing wire 140b (which is the portion of wire 30 that went under first crossing wire 140a in FIG. 6D). Wire 30 then loops around second distal pin 64b, as shown in FIG. 6G. In the embodiment shown, as wire 30 loops around second distal pin 64b, it makes an approximately 90° turn and goes over another crossing wire 142a. In the embodiment as described herein, wire 30 always goes over previously wrapped wire 142a as wire 30 loops around the nearest pin 62, 64. Wire 30 then wraps around mandrel 50 again in an upward helical fashion toward proximal pins 62 while following the angle displayed by indentations 68 until it reaches the next proximal pin 62 (e.g., third proximal pin 62c). As shown in FIG. 6H, wire 30 follows indentations 68 and goes under first crossing wire 140c (which is the portion of wire 30 that went under first crossing wire 140b in FIG. 6F).

In the illustrative embodiment, wire 30 then loops around the next proximal pin 62 (e.g., third proximal pin 62c) as shown in FIG. 6I. In this embodiment, as wire 30 loops around third proximal pin 62c, it makes an approximately 90° turn and goes over crossing wire 142b. As shown in FIG. 6J, wire 30 then wraps around mandrel 50 again in a downward helical fashion toward distal pins 64, following a set of indentations 68 until it reaches the next distal pin 64 (e.g., third proximal pin 62c). In the embodiment as shown, wire 30 goes under first crossing wire 140d (which is the portion of wire 30 that went under first crossing wire 140c in FIG. 6H). This process continues to repeat, in the embodiment shown, until wire 30 has wrapped around every proximal pin 62 and every distal pin 64.

Figure 6M:
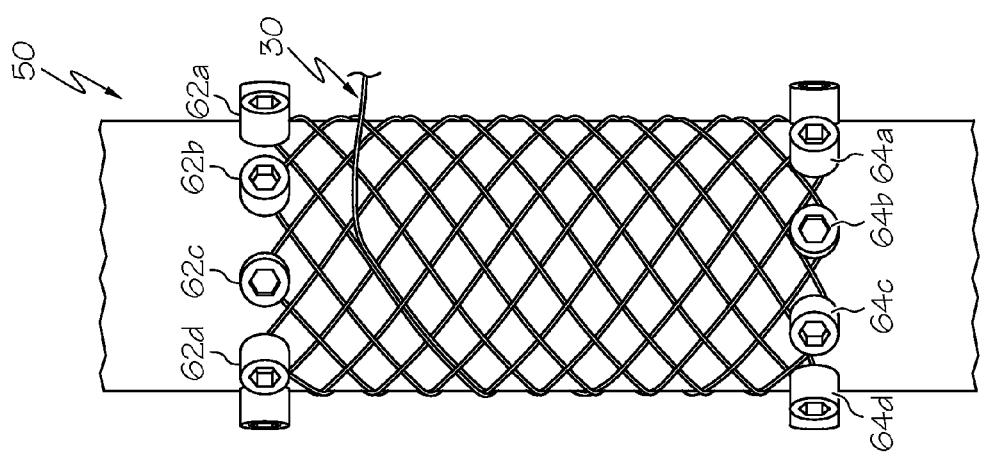

In the illustrative embodiment, once wire 30 has been wrapped around every proximal pin 62 and every distal pin 64, portion 132 of wire 30 returns toward first proximal pin 62a. In the illustrative embodiment, the portion 130 of wire 30 that was left above first proximal pin 62a in FIG. 6A is now fed backwards through the looping process, as shown in FIGS. 6K and 6L. In one embodiment, first proximal pin 62a may be loosened to allow portion 130 to be looped around first proximal pin 62a in a counterclockwise manner. Portion 130 can be slid under the first wire it encounters (as shown in FIG. 6L) and through indentation 68. Portion 130 can be woven in the same over-under pattern downward until it is at the same point as second portion 132 (or at least in close proximity thereto). Once portion 130 is at least substantially near second portion 132, portions 130 and 132 are wrapped around the mandrel together such that both portions 130 and 132 go under and over a respective crossing wire 140 together in the embodiment shown in FIG. 6M. In other embodiments, portions 130, 132 may also be fixed to one another by welding, crimping, twisting, knotting, applying adhesive or other methods of securing portions 130, 132.

After portions 130, 132 are secured, any excess wire 30 is carefully trimmed. If necessary, the stent can be heat treated while on the mandrel 50. The completed stent 10 is then removed from mandrel 50.

In some embodiments, stent removal from the mandrel 50 can be facilitated by removing the pins 58 from the mandrel 50 prior to stent removal. In some embodiments, the mandrel can be designed to allow for the pins to slide up and down a central mandrel core. The pins can be attached to a separate removable, hollow cylinder with an outer diameter equivalent to that of the mandrel. Another way to facilitate stent removal from the mandrel is to design a mandrel that allows for the distal and proximal hooks to slide up and down a central mandrel core. In this design, the hooks are attached to a separate removable, hollow cylinder with an outer diameter equivalent to that of the mandrel. Using one screw per cylinder, one cylinder is fixed to the distal end and another cylinder is fixed to the proximal end at a distance that would give the stent its overall desired length. During stent braiding, a gap is left between the braiding mandrel and part supporting the hooks. After the stent is braided and, in some embodiments, heat treated, the cylinders are unscrewed from the mandrel and moved toward the ends of the mandrel reducing the gap. This loosens the stent loops off the hooks allowing for easy stent removal as illustrated below. In some embodiments, the mandrel can consist of two parts that separate in the middle section of the stents so that the mandrel can be easily removed.

In some embodiments, it may be desirable to make retrieval loop 42 in the stent to facilitate retrieval or repositioning of stent 10, as shown in FIG. 1. The process of making retrieval loop 42, shown in FIGS. 7A-7C, occurs during the manufacturing of the stent 10 itself. In the embodiment shown in FIG. 7A, when six proximal loops 22 have been formed and as wire 30 approaches seventh proximal pin 62g, wire 30 is wrapped around seventh proximal pin 62g. However, instead of wrapping down described above, after wire 30 is wrapped around seventh proximal pin 62g, wire 30 is threaded through proximal loop 22e formed at fifth proximal pin 62e (pin shown removed in FIG. 7A for clarity). In this embodiment, wire 30 is slid under the left side of proximal loop 22e formed at fifth proximal pin 62e. A tool, such as an allen wrench, may be helpful to lift the left side of proximal loop 22e to facilitate sliding wire 30 under and through proximal loop 22e. Wire 30 can be threaded through this loop and over the right side of proximal loop 22e, as shown in FIG. 7A. Wire 30 can then be fed over the next two proximal loops 22 (i.e. at fourth proximal pin 62d and third proximal pin 62c) and then under the right side of proximal loop 22b at second proximal pin 62b, as shown in FIG. 7B. In this embodiment, wire 30 is then wrapped around mandrel 50 until it reaches seventh proximal pin 62g again, as shown in FIG. 7C. Wire 30 can then be wrapped over seventh proximal pin 62g, wrapping under the first crossing wire 150 it encounters, which in this case will be the piece of wire 30 that began retrieval loop 42. In at least one embodiment, wire 30 can then be guided down mandrel 50 toward distal pins 64 in an over under pattern and following indentations 68. After wrapping around the corresponding distal pin 64g, wire 30 may once again be guided up mandrel 50 toward proximal pins 62 according to the pattern of indentations 68. In one embodiment, as it approaches eighth proximal pin 62h, wire 30 can then be slid under retrieval loop 42 and looped around eighth proximal pin 62h and over retrieval loop 42. Wire 30 can then be guided down mandrel 50 toward distal pins 64 according to the pattern of indentations 68. In at least one embodiment, after wrapping around the corresponding distal pin 64h, wire 30 can once again be guided up mandrel 50 toward proximal pins 62 according to the pattern of indentations 68 in a helical fashion. In one embodiment, as it approaches ninth proximal pin 62i, wire 30 is guided over retrieval loop 42, around ninth proximal pin 62i, and then slid under retrieval loop 42. The braiding process may then be continued according to the embodiment shown in FIG. 6A-6M until stent 10 is completed.

In another embodiment, antimigration spikes may be formed on the sides of the stent by using a spacer, such as a screw or a bump with a cutout on the mandrel. In another embodiment, antimigration spikes can be formed on the sides of the stent by using a spacer between the surface of the mandrel and the wire to create one or several discrete spikes. The spacer can be a small rod that is introduced during the braiding process. At the completion of the braiding process and, in some embodiments, heat treat process, the rod is removed, leaving a discrete spike in the stent. Several spikes can be added to each stent. In some embodiments, antimigration spikes can also be formed by providing the mandrel with elevated bumps or raised ridges at the locations where spikes are desired in the finished stent.

Figure 8:
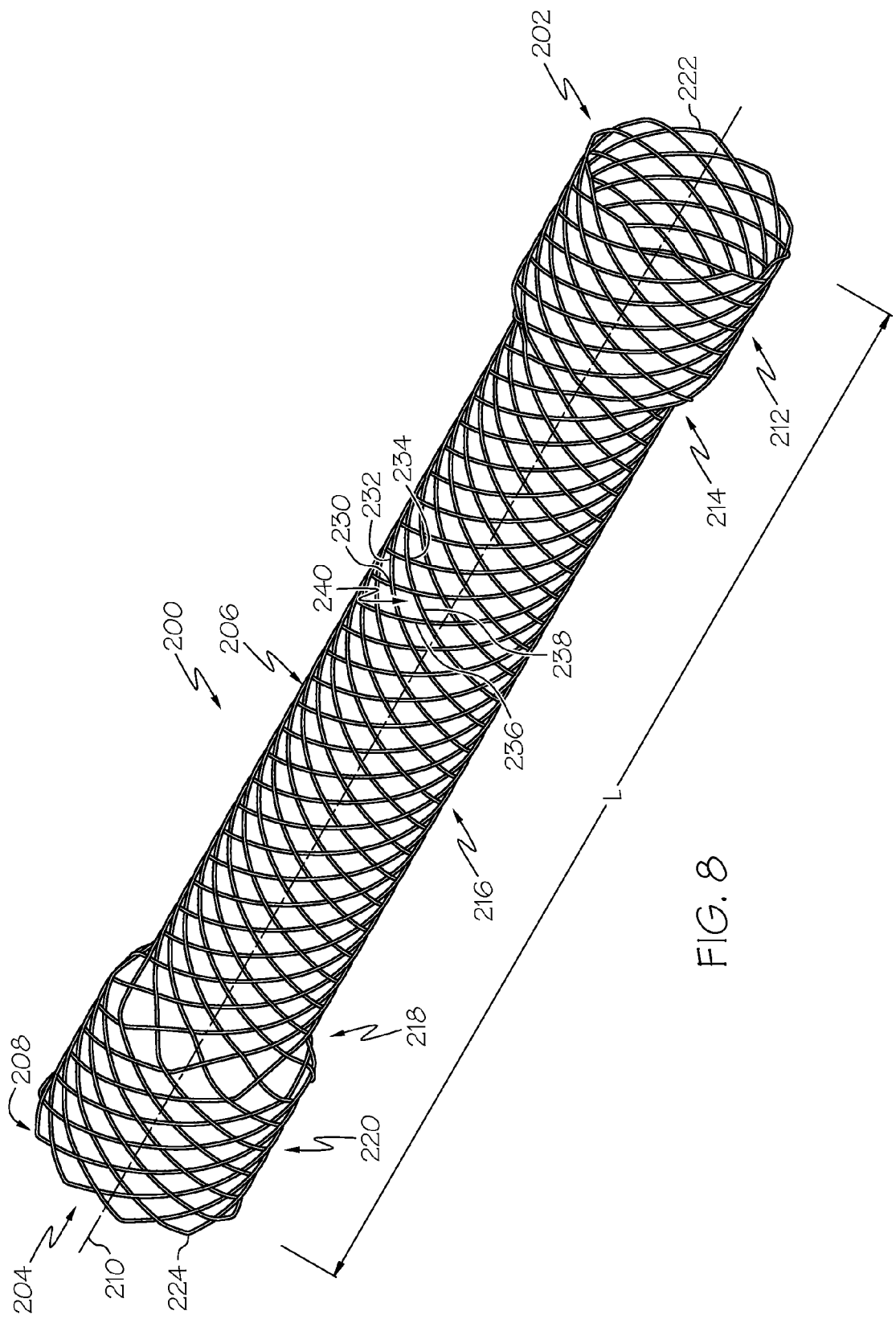
FIG. 8 is a perspective view of an embodiment of the flared stent.

In another embodiment, the present invention can be used to manufacture a flared stent 200 shown in FIG. 8. In the embodiment shown, flared stent 200 has proximal end 202, distal end 204, braided surface 206, loops 208, and longitudinal axis 210. Stent 200 can be a flared tubular member with braided surface 206 that extends along longitudinal axis 210 for a length L from proximal end 202 to distal end 204. Braided surface 206 can have proximal flared section 212, proximal transition section 214, body section 216, distal transition section 218 and distal flared section 220. A plurality of loops 208 may be formed at both proximal end 202 and distal end 204. In at least one embodiment, the total number of loops 208 may be equivalent to the total number of crossing wires in stent 200 that form braided surface 206. In one embodiment, half of loops 208 can be proximal loops 222 (located at proximal end 202) and half of loops 18 can be distal loops 224 (located at distal end 204). In at least one embodiment, proximal loops 222 are offset from distal loops 224, meaning a proximal loop 222 is not collinear with a distal loop 224 and longitudinal axis 210.

In at least one embodiment, stent 200 can be braided from a single wire 230 of material such as nitinol, PET, PTFE, and other biocompatible materials. In one embodiment, braided surface 206 can have an over-under pattern of crossing wires 232, 234, 236, 238 such that wire 230 alternates from being looped under a first crossing wire 232 to overlapping a second crossing wire 234. The intersections of crossing wires 232, 234, 236, 238 may form a diamond-like shape 240 called a lozenge. A plurality of lozenges 240 makes up braided surface 206, as shown in FIG. 8.

Figure 9:
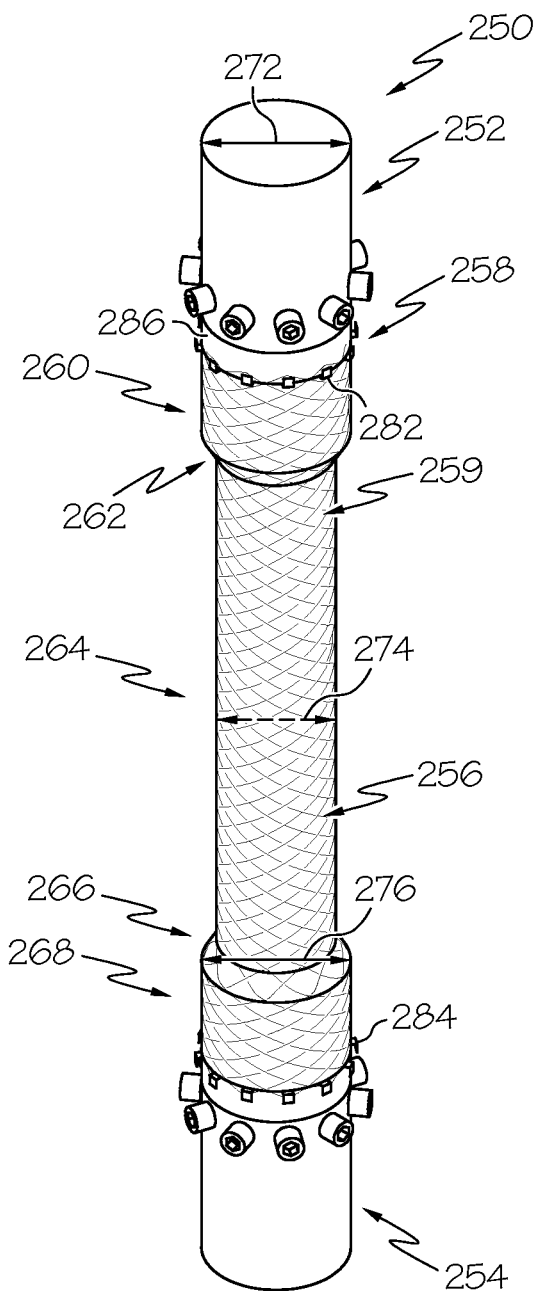
FIG. 9 is a perspective view of an embodiment of the mandrel used to form the flared stent shown in FIG. 8.

In order to manufacture flared stent 200, single wire 230 is wrapped around mandrel 250, an example of which is shown in FIG. 9. Mandrel 250 can be a cylindrical member having proximal end 252, distal end 254, outer surface 256, a plurality of pins 258, and a plurality of indentations 259. Mandrel 250 can be made of a metal, polymer, or composite material. Mandrel 250 can be a solid or hollow cylindrical member.

Like flared stent 200, mandrel 250 also can have a proximal flared section 260, proximal transition section 262, body section 264, distal transition section 268 and distal flared section 270. In the embodiment shown in FIG. 9, flared sections 260, 270 have diameter 272, body section 264 has diameter 274, and transition sections 262, 268 have an average diameter 276. To determine the proper diameter 272 for proximal flared section 260 and distal flared section 270 of mandrel 250, the following equation can be used:

$$OD_{mandrel, flared} = OD_{stent, flared} - 4d,$$

where d is the diameter (or thickness) of wire 230. It should be noted that $OD_{mandrel}$ can be measured at the bottom of the indentations. To determine the proper diameter 274 for the body section 264 of mandrel 250, the following equation can be used:

$$OD_{mandrel, body} = OD_{stent, body} - 4d.$$

Finally, to determine the proper diameter of the proximal transition section 262 and the distal transition section 268 of mandrel 250, the average of the flared diameter, $OD_{mandrel, flared}$, and the body diameter, $OD_{mandrel, body}$, can be used. In some embodiments, the desired diameter of proximal flared section 262 of stent 200 may not equal the desired diameter of distal flared section 270, and the dimensions of mandrel 250 in these embodiments may be adjusted accordingly.

In at least one embodiment, mandrel 250 may have a plurality of pins 258 circumferentially positioned on outer surface 256. A first plurality of pins 282 may be located on proximal flared section 260 ("proximal pins") and a second plurality of pins 284 is located on distal flared section 270 ("distal pins"). Pins 258 are either fixedly attached to mandrel 250 or adjustably held so that they may be loosened or tightened as needed. Pins 258 may be hooks (as shown in FIG. 9) or screws and other fasteners. In at least one embodiment, the total number of pins 258 may be equivalent to the total number of loops 208 desired on stent 200 (shown in FIG. 8). In at least one embodiment, the total number of proximal pins 282 on mandrel 250 may be equivalent to the total number of proximal loops 222 on stent 200, and the total number of distal pins 284 may be equivalent to the total number of distal loops 224 on stent 200. However, depending on the configuration of stent 10, the total number of proximal pins 282 on mandrel 250 may be greater or less than the total number of distal pins 284. In the embodiment shown in FIG. 9, distal pins 284 are rotationally offset from proximal pins 282 such that first distal pin 284a is circumferentially positioned between first proximal pin 282a and second proximal pin 282b, rather than directly aligned with either first proximal pin 282a or second proximal pin 282b. In at least one embodiment, first distal pin 284a is located at the midpoint between first proximal pin 262a and second proximal pin 282b. In at least one embodiment, distal pins 284 are rotationally offset from proximal pins 282 by an angle, which is determined by dividing 360° by the total number of pins 258. While in the embodiment shown, proximal pins 282 are all circumferentially aligned, as are distal pins 284, it is within the scope of the invention that the pins be staggered circumferentially to create staggered end loops on stent 200.

As shown in FIG. 9, mandrel 250 may use hooks as pins 258, and in particular may use hooks on a ring 286. In at least one embodiment, ring 286 can be detached from mandrel 250 to make it easier to release stent 200 from pins.

It may be desirable in some embodiments to determine the axial distance AD between proximal pins 282 and distal pins 284. The axial distance AD can be determined by the overall length L of stent 200 in a process similar to the process used to determine the axial distance for the mandrel of FIG. 2. However, here there are multiple sections of the mandrel, which makes determining the axial distance between proximal pins 282 and distal pins 284 slightly more complicated.

First, the length at the flared sections 260, 268 can be determined. For example, assuming flared section of stent 200 has a desired length of 15 mm and a lozenge axial length of 3.5 mm, the length of the flared section is divided by the lozenge axial length to calculate n, the number of lozenges 240 at flared section 260. In this case, there are 4.29 lozenges. n is then rounded to the nearest whole number, 4. To determine the axial length of flared section 200, the following equation may be used:

$$L_{flared} = (n+0.5)(L_{lozenge}) + r,$$

where r is the radius of wire 230. Only one radius is used in this equation because, in this embodiment, each flare only has loops at one of its ends, while the other end turns into the transition section and then the body section. Therefore, the actual length of each of the flared sections 260, 270 is (4.5)(3.5)+0.2=15.95 mm, assuming a wire radius of 0.2 mm.

The dimensions of transition sections 262, 266 can then be determined. For example, assuming transition section of stent 200 has a desired length of 3 mm and a lozenge axial length of 3 mm, the length of the transition section is divided by the lozenge axial length to calculate n, the number of lozenges 240 at transition section. In this case, there is 1 lozenge. n is always rounded to the nearest whole number, 1. To determine the axial length of transition section 200, the following equation may be used:

$$L_{transition} = (n)(L_{lozenge}).$$

In this embodiment, no radii are used in this equation because the transition section has no loops on either of its ends. Therefore, the actual length of the transition section, $L_{transition}$, in the example is (1)(3)=3 mm.

Finally, the dimensions at body section 264 can be determined. For example, assuming body section of stent 200 has a desired length of 110 mm and a lozenge axial length of 2.7 mm, the length of the body section is divided by the lozenge axial length to calculate n, the number of lozenges 140 at body section 264. In this case, there are 40.74 lozenges. n is then rounded to the nearest whole number, 41. To determine the axial length of body section 264, the following equation may be used:

$$L_{body} = (n+0.5)(L_{lozenge})$$

Just like the calculation for transition sections 262, 266, no radii are used in this equation because body section 264 has no loops 208 on either of its ends. Therefore, the actual length of the body section 264 is (41.5)(2.7)=112.05 mm.

Thus, in at least one embodiment, the actual overall length of stent 200 can be the sum of the length of each section $L_{flared}$, $L_{transition}$ and $L_{body}$. In one embodiment of the invention, the axial distance AD between proximal pins 282 and distal pins 284 can then be calculated by subtracting two wire radii and two pin hole radii from the actual overall length $L_{actual}$.

In at least one embodiment of the invention, the process for manufacturing the flared stent 200 follows the process discussed above with respect to stent 10. Wire 230 may be attached to a screw at the top of mandrel 250 and then wound down in a helical fashion past one hook determined to be the starting pin 282a. In one embodiment, wire 230 is wound down and around mandrel 250, following the pattern of indentations 259 in mandrel 250 until it reaches distal pins 284. Wire 230 can then be wound up and around mandrel 250, again following the grooved pattern of indentations 259 until it reaches proximal pins 282. In at least one embodiment, wire 230 can continue to be looped in this manner until the stent is completely braided, as shown in FIGS. 6A-6N. In at least one embodiment, an integral retrieval loop or anti-migration spikes may also be formed in flared stent 200 as previously discussed above.

In some embodiments, stent removal from the mandrel 250 can be facilitated by removing the pins 282, 284 from the mandrel 250 prior to stent removal. In some embodiments, the mandrel can be designed to allow for the pins or hooks or other fasteners to slide up and down a central mandrel core. The pins or hooks or other fasteners can be attached to a separate removable, hollow cylinder with an outer diameter equivalent to that of the mandrel. Another way to facilitate stent removal from the mandrel is to design a mandrel that allows for the distal and proximal fasteners to slide up and down a central mandrel core. In this design, each pin, hook, or other fastener is attached to a separate removable, hollow cylinder with an outer diameter equivalent to that of the proximal or distal flared sections. Using one screw per cylinder, one cylinder is fixed to the distal end and another cylinder is fixed to the proximal end at a distance that would give the stent its overall desired length. During stent braiding, a gap is left between the braiding mandrel and part supporting the hooks. After the stent is braided and heat treated, the part supporting the hooks are unscrewed from the body section and moved toward the flared sections reducing the gap. This loosens the stent loops off the pins or hooks allowing for easy stent removal. In some embodiments, the mandrel can consist of two parts that separate in the middle section of the stents so that the mandrel can be easily removed from a double flare stent.

In some embodiments, repositioning or removal sutures can be provided. In some embodiments, other surface modifications can be made to the surface of the mandrel depending on certain characteristics desired in the completed stent. In some embodiments, the mandrel can be used with multiple wires.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 2; claim 4 may be taken as alternatively dependent on claim 2, or on claim 3; claim 6 may be taken as alternatively dependent from claim 5; etc.).

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method of manufacturing a single-wire stent having a proximal end, a distal end, a diameter, a length, a plurality of loops on the proximal end, and a plurality of loops on the distal end, the method comprising:
    (a) securing a single wire to a mandrel, the mandrel having proximal pins positioned in a proximal end region of the mandrel, distal pins positioned in a distal end region of the mandrel, and indentations between the proximal pins and the distal pins on an outer surface of the mandrel, the proximal and distal pins having a total number, wherein there is a rotational offset between the proximal and distal pins so that each distal pin is circumferentially positioned between two proximal pins, the rotational offset being equal to a division of 360° by the total number of proximal and distal pins;
    (b) wrapping the single wire around a first proximal pin and down the mandrel in a downward helical direction by following a first plurality of indentations until the single wire reaches a first distal pin;
    (c) wrapping the single wire around the first distal pin and up the mandrel in an upward helical direction by following a second plurality of indentations in the mandrel until the single wire reaches a second proximal pin, sliding the single wire under a first crossing section of wire;
    (d) repeating steps (b) and (c) until the single wire has wrapped around every proximal pin and distal pin on the mandrel by following the indentations in the mandrel, sliding the single wire under at least the first crossing section of wire and over at least a second crossing section of wire in an under-over pattern;
    (e) securing ends of the single wire after the single wire has wrapped around every proximal pin and every distal pin.

2. The method of claim 1, wherein securing ends of the single wire comprises:
    wrapping a first end of the single wire around the first proximal pin;
    wrapping the first end of the single wire around the mandrel in a helical direction by following the indentations in the mandrel in an over-under pattern until it reaches a location of a second end of the single wire;
    wrapping the first end of the single wire together with the second end of the single wire around the mandrel in the helical direction in the over-under pattern; and
    trimming any excess of the single wire.

3. The method of claim 1, further comprising:
    (f) forming an integral retrieval loop after the single wire has wrapped around some but not all of the proximal pins and some but not all of the distal pins.

4. The method of claim 3, wherein forming the integral retrieval loop comprises:
    wrapping the single wire around an initial proximal pin;
    threading the single wire through a loop formed at a previous proximal pin;

threading the single wire through a loop formed at a second previous proximal pin;

wrapping the single wire around a circumference of the mandrel until it reaches the initial proximal pin; and wrapping the single wire over the initial proximal pin and then under a previously wrapped section of wire; and continuing with step (d) until the single wire has wrapped around every proximal pin and distal pin.

5. The method of claim 1, further comprising:
(f) removing a finished stent from the mandrel.

6. The method of claim 1, wherein at least a portion of the stent is annealed.

7. The method of claim 1, wherein securing the stent comprises fixing a first end of the single wire to a second end of the single wire by welding, crimping, twisting, knotting, applying adhesive or other methods.

8. The method of claim 1, wherein the stent is a flared stent.

9. The method of claim 1, wherein a displacement between the first proximal pin and the first distal pin has a magnitude, where the magnitude and the total number of proximal and distal pins are coprime numbers.

10. The method of claim 1, wherein the indentations are elongated and oriented in either the downward helical direction or the upward helical direction, wherein the elongated indentations define crossing points for the single wire, each crossing point defined by three separate elongated indentations, wherein two of the three elongated indentations are aligned in one of the upward or downward helical directions and one of the three elongated indentations is positioned between the two elongated indentations and oriented in the other of the upward or downward helical directions.

11. The method of claim 1, wherein the indentations are elongated and oriented in either the downward helical direction or the upward helical direction, wherein sliding the single wire comprises sliding the single wire through one of the elongated indentations located underneath the first crossing section of wire, the first crossing section of wire extending in a helical direction opposite to the helical direction of the elongated indentation positioned underneath.

12. The method of claim 1, wherein the indentations hold the single wire in place as the single wire is being wrapped around the mandrel.

13. A method of manufacturing a single-wire stent having a proximal end, a distal end, a diameter, a length, a plurality of loops on the proximal end, and a plurality of loops on the distal end, the method comprising:
(a) securing a single wire to a mandrel, the mandrel having proximal pins, distal pins, and elongated indentations between the proximal pins and the distal pins on an outer surface of the mandrel, the elongated indentations aligned into helical pathways where a helical pathway is oriented in either an upward or a downward helical direction, each helical pathway comprising a plurality of the elongated indentations, wherein the elongated indentations define crossing points for the single wire, each crossing point defined by three separate elongated indentations, with two of the three elongated indentations aligned in one of the upward or downward helical directions and the third elongated indentation is positioned between the two elongated indentations and oriented in the other of the upward or downward helical directions, the third elongated indentation providing a channel for the single wire to slide under a crossing section of wire;
(b) wrapping the single wire around a first proximal pin and down the mandrel along a downward helical pathway until the single wire reaches a first distal pin;
(c) wrapping the single wire around the first distal pin and up the mandrel along an upward helical pathway direction until the single wire reaches a second proximal pin, sliding the single wire under a first crossing section of wire;
(d) repeating steps (b) and (c) until the single wire has wrapped around every proximal pin and distal pin on the mandrel by following the helical pathways formed by the elongated indentations in the mandrel, sliding the single wire under at least the first crossing section of wire and over at least a second crossing section of wire in an under-over pattern;
(e) securing ends of the single wire after the single wire has wrapped around every proximal pin and every distal pin.

14. The method of claim 13, wherein the distal pins are rotationally offset from the proximal pins so that each distal pin is circumferentially positioned between two proximal pins, the rotational offset being equal to a division of 360° by the total number of proximal and distal pins.

15. The method of claim 13, wherein each indentation does not intersect with any other indentation.

16. A method of manufacturing a single-wire stent having a proximal end, a distal end, a diameter, a length, a plurality of loops on the proximal end, and a plurality of loops on the distal end, the method comprising:
(a) securing a single wire to a mandrel, the mandrel having proximal pins positioned in a proximal end region of the mandrel, distal pins positioned in a distal end region of the mandrel, and indentations extending longitudinally in a helical direction between the proximal pins and the distal pins on an outer surface of the mandrel;
(b) wrapping the single wire around a first proximal pin and down the mandrel in a downward helical direction by following a first plurality of indentations until the single wire reaches a first distal pin;
(c) wrapping the single wire around the first distal pin and up the mandrel in an upward helical direction by following a second plurality of indentations in the mandrel until the single wire reaches a second proximal pin, sliding the single wire under a first crossing section of wire;
(d) forming an integral retrieval loop after the single wire has wrapped around some but not all the proximal pins and some but not all of the distal pins;
(e) repeating steps (b) and (c) until the single wire has wrapped around every proximal pin and distal pin on the mandrel by following the indentations in the mandrel, sliding the single wire under at least the first crossing section of wire and over at least a second crossing section of wire in an under-over pattern; and
(f) securing ends of the single wire after the single wire has wrapped around every proximal pin and every distal pin.

17. The method of claim 16, wherein each indentation is adapted to laterally secure a portion of the single wire when the single wire is positioned within the indentation.

* * * * *